(12) United States Patent
Nappa

(10) Patent No.: US 8,445,735 B2
(45) Date of Patent: May 21, 2013

(54) CONVERSION OF 2-CHLORO-1,1,1,2-TETRAFLUOROPROPANE TO 2,3,3,3-TETRAFLUOROPROPENE

(75) Inventor: Mario Joseph Nappa, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/478,253

(22) Filed: May 23, 2012

(65) Prior Publication Data

US 2012/0232316 A1    Sep. 13, 2012

Related U.S. Application Data

(63) Continuation of application No. 12/605,573, filed on Oct. 26, 2009, now Pat. No. 8,203,022.

(60) Provisional application No. 61/108,585, filed on Oct. 27, 2008, provisional application No. 61/121,248, filed on Dec. 10, 2008.

(51) Int. Cl.
*C07C 17/25* (2006.01)

(52) U.S. Cl.
USPC .......................................... 570/155; 570/136

(58) Field of Classification Search
None
See application file for complete search history.

(56) References Cited

U.S. PATENT DOCUMENTS

| | | | |
|---|---|---|---|
| 5,516,946 A | 5/1996 | Jackson et al. | |
| 7,294,747 B2 | 11/2007 | Bonnet | |
| 2005/0070746 A1 * | 3/2005 | Tung et al. | 570/155 |
| 2006/0094911 A1 * | 5/2006 | Rao et al. | 570/155 |
| 2007/0197842 A1 | 8/2007 | Mukhopadhyay et al. | |
| 2009/0030247 A1 | 1/2009 | Johnson et al. | |
| 2009/0149680 A1 | 6/2009 | Wang et al. | |

FOREIGN PATENT DOCUMENTS

| | | |
|---|---|---|
| EP | 407711 A1 | 1/1991 |
| WO | 2008002499 A2 | 1/2008 |

* cited by examiner

*Primary Examiner* — Sudhakar Katakam

(57) ABSTRACT

Described is a method for producing fluoropropenes of formula $CF_3CX=CX_2$ wherein each X is F or H, at least one X is H, and at least one X is F, comprising pyrolyzing a hydrofluorochloropropane of formula $CF_3CXYCX_2Y$, wherein each X is F or H, at least one X is H, and at least one X is F, and one Y is Cl and the other Y is H, in the gas-phase in a reaction vessel, maintained at a temperature high enough to effect the pyrolysis of said hydrofluorochloropropane to said fluoropropene, wherein the selectivity for the production of the fluoropropene is at least 80%, in he absence of a catalyst.

11 Claims, No Drawings

CONVERSION OF 2-CHLORO-1,1,1,2-TETRAFLUOROPROPANE TO 2,3,3,3-TETRAFLUOROPROPENE

CROSS REFERENCE(S) TO RELATED APPLICATION(S)

This application is a continuation of pending U.S. application Ser. No. 12/605,573, filed Oct. 26, 2009, which claims the benefit of priority of U.S. Provisional Applications 61/108,585, filed Oct. 27, 2008, and 61/121,248, filed Dec. 10, 2008.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

Described is a method for producing fluoropropenes of formula $CF_3CX=CX_2$ wherein each X is F or H, at least one X is H, and at least one X is F, comprising pyrolyzing a hydrofluorochloropropane of formula $CF_3CXYCX_2Y$, wherein each X is F or H, at least one X is H, and at least one X is F, and one Y is Cl and the other Y is H, in the gas-phase in a reaction vessel, maintained at a temperature high enough to effect the pyrolysis of said hydrofluorochloropropane to said fluoropropene, wherein the selectivity for the production of the fluoropropene is at least 80%, in the absence of a catalyst.

The foregoing general description and the following detailed description are exemplary and explanatory only and are not restrictive of the invention, as defined in the appended claims.

DETAILED DESCRIPTION

Described is a method for producing fluoropropenes of formula $CF_3CX=CX_2$ wherein each X is F or H, at least one X is H, and at least one X is F, comprising pyrolyzing a hydrofluorochloropropane of formula $CF_3CXYCX_2Y$, wherein each X is F or H, at least one X is H, and at least one X is F, and one Y is Cl and the other Y is H, in the gas-phase in a reaction vessel, maintained at a temperature high enough to effect the pyrolysis of said hydrofluorochloropropane to said fluoropropene, wherein the selectivity for the production of the fluoropropene is at least 80%, in the absence of a catalyst.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

As used herein, the terms pyrolyzing and pyrolysis refer to the decomposition or breaking down of a material or compound due to heat in the absence of oxygen or any other reagents.

As used herein, reaction vessel refers to any vessel in which the reaction may be performed in either a batchwise mode, or in a continuous mode. Suitable vessels include batch reactor vessels, or tubular reactors.

In one embodiment, the reaction vessel is comprised of materials which are resistant to corrosion including stainless steel, Hastelloy, Inconel, Monel, gold, or gold-lined or quartz.

As used herein, percent selectivity is defined as the weight of a desired product formed, as a fraction of the total amount of the products formed in the reaction, and excluding the starting chlorofluorocarbon.

As used herein, percent conversion is defined as 100%, less the weight percent of starting hydrofluorochloropropane in the effluent from the reaction vessel.

The hydrochlorofluoropropane described herein has the formula $CF_3CXYCX_2Y$, wherein each X is F or H, at least one X is H, and at least one X is F, and one Y is Cl and the other Y is H. A fluoropropene as described herein has the formula $CF_3CX=CX_2$ wherein each X is F or H, at least one X is H, and at least one X is F. Representative hydrochlorofluoropropanes include 1,1,1,2-tetrafluoro-2-chloropropane, 1,1,1,2-tetrafluoro-3-chloropropane, 1,1,1,3-tetrafluoro-2-chloropropane, 1,1,1,3-tetrafluoro-3-chloropropane, 1,1,1,2,3-pentafluoro-2-chloropropane, 1,1,1,2,3-pentafluoro-3-chloropropane, 1,1,1,3,3-pentafluoro-2-chloropropane and 1,1,1,3,3-pentafluoro-3-chloropropane.

Representative fluoropropenes include 2,3,3,3-tetrafluoropropene, 1,3,3,3-tetrafluoropropene, 1,2,3,3,3-pentafluoropropene and 1,1,3,3,3-pentafluoropropene.

In one embodiment, the hydrochlorofluoropropane is 1,1,1,2-tetrafluoro-2-chloropropane and the fluoropropene is 2,3,3,3-tetrafluoropropene. In another embodiment, the hydrochlorofluoropropane is 1,1,1,2-tetrafluoro-3-chloropropane and the fluoropropene is 2,3,3,3-tetrafluoropropene. In yet another embodiment, the hydrochlorofluoropropane is 1,1,1,3-tetrafluoro-2-chloropropane and the fluoropropene is 1,3,3,3-tetrafluoropropene. In yet another embodiment, the hydrochlorofluoropropane is 1,1,1,3-tetrafluoro-3-chloropropane and the fluoropropene is 1,3,3,3-tetrafluoropropene. In yet another embodiment, the hydrochlorofluoropropane is 1,1,1,2,3-pentafluoro-2-chloropropane and the fluoropropene is 1,2,3,3,3-pentafluoropropene. In yet another embodiment, the hydrochlorofluoropropane is 1,1,1,2,3-pentafluoro-3-chloropropane and the fluoropropene is 1,2,3,3,3-pentafluoropropene. In yet another embodiment, the hydrochlorofluoropropane is 1,1,1,3,3-pentafluoro-2-chloropropane and the fluoropropene is 1,1,3,3,3-pentafluoropropene. In yet another embodiment, the hydrochlorofluoropropane is 1,1,1,3,3-pentafluoro-3-chloropropane and the fluoropropene is 1,1,3,3,3-pentafluoropropene.

In one embodiment, fluoropropenes are prepared by thermal dehydrochlorination of hydrochlorofluoropropanes. This reaction occurs selectively, in the absence of a catalyst. In one embodiment, a hydrochlorofluoropropane is introduced into a reaction vessel wherein the temperature is maintained at a temperature high enough to effect the thermal dehydrochlorination of the hydrochlorofluoropropane. In one embodiment, the temperature is high enough to effect the thermal dehydrochlorination of the hydrochlorofluoropropane to a percent conversion of at least 50%. In another embodiment, the temperature is high enough to effect the thermal dehydrochlorination of the hydrochlorofluoropropane to a percent conversion of at least 65%. In yet another embodiment, the temperature is high enough to effect the thermal dehydrochlorination of the hydrochlorofluoropropane to a percent conversion of at least 80%. In yet another embodiment, the temperature is high enough to effect the thermal dehydrochlorination of the hydrochlorofluoropropane to a percent conversion of at least 70% for at least 12 hours of continuous operation.

In one embodiment, the hydrochlorofluoropropane is introduced into a reaction vessel wherein the temperature is maintained at a temperature in the range of from about 500° C. to about 700° C. In another embodiment, the temperature of the reaction vessel is maintained in the range from about 500° C. to about 650° C. In yet another embodiment, the temperature of the reaction vessel is maintained at a temperature high enough to effect the pyrolysis of the hydrochlorofluoropropane to fluoropropene with a selectivity of 80% or greater. In yet another embodiment, the temperature of the reaction vessel is maintained at a temperature high enough to effect the pyrolysis of the hydrochlorofluoropropane to the fluoropropene with a selectivity of 85% or greater.

In one embodiment, the reaction vessel is comprised of materials which are resistant to corrosion. In one embodiment, these materials comprise alloys, such as stainless steel, Hastelloy, Inconel, Monel, and gold, gold-lined or quartz.

In one embodiment, the hydrochlorofluoropropane is preheated in a vaporizer to a temperature of from about 30° C. to about 100° C. In another embodiment, the hydrochlorofluoropropane is preheated in a vaporizer to a temperature of from about 30° C. to about 80° C.

In some embodiments, an inert diluent gas is used as a carrier gas for the hydrochlorofluoropropane. In one embodiment, the carrier gas is selected from nitrogen, argon, helium or carbon dioxide.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Legend
HFC-244bb is 2-chloro-1,1,1,2-tetrafluoropropane
HFO-1234yf is 2,3,3,3-tetrafluoropropene
HCFO-1233xf is 2-chloro-3,3,3-trifluoropropene Example 1

Example 1 demonstrates the conversion of 2-chloro-1,1,1,2-tetrafluoropropane to 2,3,3,3-tetrafluoropropene in the absence of a catalyst.

An empty inconel tube (½ inch OD) with a heated zone of about 12 inches was heated to a temperature between 500° C. and 626° C., and HFC-244bb was fed at 0.52 ml/hour through a vaporizer set at 40° C. using a $N_2$ sweep of 2.4 sccm (4.0× $10^{-8}$ $m^3$). The reactor effluent was analyzed using an on-line GCMS, with the results being reported in mole percent. Results for percent conversion, percent selectivity, and operating temperature are reported in Table 1, below.

TABLE 1

| Temp ° C. | Conversion of 244bb | Selectivity to 1234yf | Selectivity to 1233xf |
|---|---|---|---|
| 500 | 16.2% | 80% | 8% |
| 550 | 65.4% | 88% | 2% |
| 574 | 86.4% | 88% | 2% |
| 601 | 99.6% | 85% | <1% |
| 626 | 99.8% | 83% | 1% |

Example 2

Example 2 demonstrates the conversion of 2-chloro-1,1,1,2-tetrafluoropropane to 2,3,3,3-tetrafluoropropene in the absence of a catalyst.

An empty inconel tube (½ inch OD) with a heated zone of about 12 inches was heated to 575° C., and HFC-244bb was fed at 0.35 ml/hour through a vaporizer set at 40° C. using a $N_2$ sweep of 3.6 sccm (6.0×$10^{-8}$ $m^3$). The reactor was operated for a total of 19 hours continuously, and samples were taken periodically and analyzed to determine % conversion of HFC-244bb, and selectivity to HFO-1234yf. The reactor effluent was analyzed using an on-line GCMS, and the data in Table 2 below is an average of at least two on-line injections at a given condition; the percentages are mole percent. The data in Table 2 show the performance of this reaction to make HFO-1234yf via HCl elimination over the period of 19 hours of operation.

TABLE 2

| Hours | Conversion of 244bb | Selectivity to 1234yf | Selectivity to 1233xf |
|---|---|---|---|
| 3 | 80% | 84% | 6% |
| 4 | 75% | 80% | 9.7% |
| 8 | 81% | 72% | 17% |
| 12 | 81% | 70% | 20% |
| 15 | 82% | 78% | 14% |
| 19 | 85% | 73% | 19.6% |

Example 3

Example 3 demonstrates the conversion of 2-chloro-1,1,1,2-tetrafluoropropane to 2,3,3,3-tetrafluoropropene in the absence of a catalyst in a gold-lined tube.

An empty gold-lined tube (½ inch OD) with a heated zone of about 12 inches was heated to a temperature about 550° C., and HFC-244bb was fed at 0.75 ml/hour through a vaporizer set at 40° C. using a $N_2$ sweep of 3.75 sccm ($6.25 \times 10^{-8}$ $m^3$). The reactor effluent was analyzed using an on-line GCMS, with the results being reported in mole percent. Results for percent conversion, percent selectivity, and operating temperature are reported in Table 3, below.

TABLE 3

| Temp ° C. | Conversion of 244bb | Selectivity to 1234yf | Selectivity to 1233xf |
|---|---|---|---|
| 550 | 72% | 94% | 2% |

Comparative Example 1

Comparative Example 1 demonstrates the dehydrochlorination of 2-chloro-1,1,1,2-tetrafluoropropane in the presence of an activated carbon catalyst.

An inconel tube (½ inch OD) was filled with 4 cc (1.99 gm) of acid washed PCB Polynesian coconut shell based carbon from Calgon (6-10 mesh). HFC-244bb was fed at 1.04 ml/hour through a vaporizer set at 40° C. using a $N_2$ sweep of 2.4 sccm ($4.0 \times 10^{-8}$ $m^3$) giving a total contact time of about 32 seconds while controlling the reactor temperature at 400° C.

The data in Table 4 show the performance of this process with an activated carbon catalyst to make HFO-1234yf via HCl elimination over the period of 15 hours of operation.

TABLE 4

| Hours | conversion of 244bb | selectivity 1234yf | selectivity 1233xf |
|---|---|---|---|
| 1 | 78% | 67% | 13% |
| 2 | 75% | 59% | 18% |
| 3 | 68% | 56% | 22% |
| 4 | 58% | 44% | 27% |
| 5 | 51% | 31% | 35% |
| 6 | 46% | 15% | 39% |
| 7 | 46% | 6% | 38% |
| 8 | 47% | 3% | 32% |
| 9 | 45% | 2% | 29% |
| 10 | 31% | 3% | 36% |
| 11 | 21% | 5% | 64% |
| 12 | 23% | 5% | 66% |
| 13 | 24% | 5% | 67% |
| 14 | 24% | 6% | 73% |
| 15 | 23% | 6% | 72% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A method for producing a fluoropropene of formula $CF_3CX=CX_2$ wherein each X is F or H, at least one X is H, and at least one X is F, comprising:
   pyrolyzing a hydrofluorochloropropane of formula $CF_3CXYCX_2Y$, wherein each X is F or H, at least one X is H, and at least one X is F, and one Y is Cl and the other Y is H, and where the hydrofluorochloropropane is not $CF_3CFClCH_3$, in the gas-phase in a reaction vessel, maintained at a temperature high enough to effect the pyrolysis of said hydrofluorochloropropane to said fluoropropene, wherein the selectivity for the production of the fluoropropene is at least 80%, in the absence of a catalyst.

2. The method of claim 1 wherein, said selectivity for the production of said fluoropropene is at least 80% after about 4 hours of continuous operation.

3. The method of claim 1 wherein, said selectivity for the production of said fluoropropene is at least 70% after about 12 hours of continuous operation.

4. The method of claim 1 wherein, the temperature of the reaction vessel is maintained in the range from about 500° C. to about 700° C.

5. The method of claim 1, wherein said selectivity for the production of said fluoropropene is at least 85%.

6. The method of claim 1, wherein the said hydrofluorochloropropane is preheated in a vaporizer at a temperature of from about 30° C. to about 100° C.

7. The method of claim 1, wherein the said hydrofluorochloropropane fed to the reaction vessel further comprises an inert carrier gas.

8. The method of claim 7 wherein the inert carrier gas is chosen from nitrogen, argon, helium or carbon dioxide.

9. The method of claim 1, wherein the temperature of the reaction vessel is maintained in the range from about 500° C. to about 650° C.

10. The method of claim 1, wherein the hydrofluorochloropropane is selected from the group consisting of 1,1,1,2-tetrafluoro-3-chloropropane, 1,1,1,3-tetrafluoro-2-chloropropane, 1,1,1,3-tetrafluoro-3-chloropropane, 1,1,1,2,3-pentafluoro-2-chloropropane, 1,1,1,2,3-pentafluoro-3-chloropropane, 1,1,1,3,3-pentafluoro-2-chloropropane and 1,1,1,3,3-pentafluoro-3-chloropropane.

11. The method of claim 1, wherein the hydrofluorochloropropane is 1,1,1,3-tetrafluoro-3-chloropropane.

* * * * *